(12) United States Patent
Kunitomi et al.

(10) Patent No.: US 7,377,911 B2
(45) Date of Patent: *May 27, 2008

(54) MEDICAL NEEDLE DEVICE WITH WINGED SHIELD FOR ERRONEOUS PIERCING PREVENTION

(75) Inventors: Jun Kunitomi, Minato (JP); Takashi Doi, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 319 days.

This patent is subject to a terminal disclaimer.

(21) Appl. No.: 10/479,691

(22) PCT Filed: Oct. 7, 2002

(86) PCT No.: PCT/JP02/10424

§ 371 (c)(1),
(2), (4) Date: Dec. 5, 2003

(87) PCT Pub. No.: WO03/033056

PCT Pub. Date: Apr. 24, 2003

(65) Prior Publication Data

US 2004/0147882 A1  Jul. 29, 2004

(30) Foreign Application Priority Data

Oct. 10, 2001 (JP) ............................ 2001-312342

(51) Int. Cl.
*A61M 5/32* (2006.01)
(52) U.S. Cl. ..................................................... 604/177
(58) Field of Classification Search ................ 604/263, 604/272, 177, 164.02, 164.03, 164.04, 110, 604/164.08, 171, 165.03
See application file for complete search history.

(56) References Cited

U.S. PATENT DOCUMENTS

| | | | | |
|---|---|---|---|---|
| 3,538,915 A | * | 11/1970 | Frampton et al. | ........... 604/272 |
| 3,640,275 A | | 2/1972 | Burke et al. | |
| 4,192,304 A | | 3/1980 | Millet | |
| 4,194,504 A | * | 3/1980 | Harms et al. | .......... 604/165.03 |
| 5,085,639 A | | 2/1992 | Ryan | |

(Continued)

FOREIGN PATENT DOCUMENTS

| | | |
|---|---|---|
| AU | 200074450 | 4/2001 |
| EP | 0 253 990 | 1/1988 |
| EP | 0 566 769 | 4/1992 |

(Continued)

*Primary Examiner*—Kevin Sirmons
*Assistant Examiner*—Catherine N Witczak
(74) *Attorney, Agent, or Firm*—Hamre, Schumann, Mueller & Larson, P.C.

(57) ABSTRACT

A medical needle device includes a winged shield (4) having a substantially cylindrical shaped shield cylinder (4*a*) and wings (5, 6) connected to the front end side thereof, a needle base (2) inserted in the shield cylinder (4*a*), and a needle (1). The wings have wing projections (7, 8) and the shield cylinder has through holes (9, 10) on the wall thereof. By overlaying the wings along the side surface of the shield cylinder, each of the wing projections can be inserted into the inner cavity of the shield cylinder via the through hole. Thereby, without requiring a special operation in the sticking operation, each of the wing projections can prevent the needle base from moving in the axial direction and can hold the needle base in the shield cylinder reliably in a state in which the needle protrudes from the front end of the shield cylinder by a predetermined length.

10 Claims, 9 Drawing Sheets

U.S. PATENT DOCUMENTS

| | | |
|---|---|---|
| 5,088,982 A | 2/1992 | Ryan |
| 5,382,240 A | 1/1995 | Lam |
| 5,779,679 A * | 7/1998 | Shaw .................... 604/158 |
| 5,928,199 A | 7/1999 | Nakagami |

FOREIGN PATENT DOCUMENTS

| | | | |
|---|---|---|---|
| EP | 0 732 119 | | 9/1996 |
| EP | 1 402 911 | | 10/2002 |
| JP | 1-212561 | | 8/1989 |
| JP | 6-7861 | | 8/1989 |
| JP | 6-7442 | | 1/1994 |
| JP | 7-75671 | | 3/1995 |
| JP | 2001-252356 | | 9/2001 |
| WO | 91/04761 | | 4/1991 |
| WO | WO 94/11050 | * | 5/1994 |
| WO | WO 01/23021 | | 4/2001 |
| WO | 02/26284 | | 4/2002 |

* cited by examiner

FIG. 10

MEDICAL NEEDLE DEVICE WITH WINGED SHIELD FOR ERRONEOUS PIERCING PREVENTION

This application is 371 of international application PCT/JP02/10424 filed Oct. 7, 2002, which claims the priority of Japanese Application No. 2001-312342 filed Oct. 10, 2001.

TECHNICAL FIELD

The present invention relates to winged medical needle devices, and more particularly to medical needle devices having a winged shield for the reduction of needle-stick injuries, in which the cannula can be stored away safely after use.

BACKGROUND ART

Conventionally, contamination and infections due to needle-stick injuries with injection needles or puncture needles have been a problem in medical facilities. In particular recently, as hepatitis B, hepatitis C and HIV (human immunodeficiency virus) have become widespread throughout the population, there is a strong demand for means that actively prevent accidental needle-stick injuries.

As a means for preventing needle-stick injuries, various injection needle devices have been proposed, in which the cannula is covered by a cover when collecting injection needles or puncture needles after use. Most of such means for reduction of needle-stick injuries have a cylindrical protection cover (referred to as "shield" in the following) for preventing needle-stick injuries after use, and this shield can slide with respect to the injection needle. That is to say, depending on the sliding state of the shield, the injection needle is either exposed or it is covered by the shield.

On the other hand, for measures such as the infusions or blood transfusions, or extracorporeal blood circulation, winged infusion needle devices are used widely. Winged infusion needle devices have a structure in which wings are mounted on a hub, in which the infusion needle is fixed at the front, and whose rear is connected to an infusion tube. Thus, the means for preventing needle-stick injuries with a winged injection needle device necessitates a special structure. That is to say, the structure has to be such that the wings do not obstruct the sliding of the shield. For this reason, conventional structures are classified into types in which the wings are attached to the infusion needle or the hub and types in which the wings are attached to the shield.

Examples of the latter structure are described for example in JP H06-7861B, WO 91/04761 or U.S. Pat. No. 5,088,982. In these conventional examples, the wings are attached to the outer peripheral surface of a slidable tubular shield, and the wings slide together with the shield on the outer side of the infusion needle. In order to prevent needle-stick injuries after use of the infusion needle, the tip of the infusion needle can be covered by sliding the shield.

In the course of using such an infusion needle device in which wings are attached to the shield, a mechanism is necessary for holding the infusion needle temporarily at a predetermined position with respect to the shield and fitting the two together. Furthermore, it is desirable that the effect of holding the needle with respect to the shield differs during the puncturing action and during the storage action of storing the injection needle in the shield for the sake of preventing needle-stick injuries, as described below.

When performing a puncturing action, the shield is grasped to perform the action, so that it is necessary that the needle is held securely by the shield. On the other hand, when performing the action of storing the needle away, the force for holding the shield should be rather weak in order to make easy the operation therefore. When the holding force is too strong, then the action of sliding the needle within the shield becomes difficult, and there is the risk that it may lead to unexpected accidents. On the other hand, when the needle is retained on the patient, the shield is fastened to the patient's skin near the punctured portion, so that if the needle is easily moved within the shield in this situation, there is the risk that the needle is easily pulled out from the patient. Consequently, it is inconvenient if the holding force is too weak during needle retention. In conclusion, it is preferable that after the puncturing action, a suitable holding force weaker than that at the time of the puncturing action acts on the injection needle or the hub.

However, in conventional injection needle devices having a winged shield, the holding of the injection needle at the time of the puncturing action and after the puncturing action (i.e. during retention and during removal of the needle) is performed by the same mechanism, and a suitable holding force could not be attained for both the puncturing action and the storing action.

Consequently, it is an object of the present invention to provide a medical needle device, in which both during the puncturing action and after the puncturing action, the medical needle can be held with optimum holding power with respect to a winged shield, and with which the action of storing the medical needle into the shield after use can be performed safely and easily.

DISCLOSURE OF INVENTION

In a basic configuration of the present invention, a medical needle device includes a winged shield for reduction of needle-stick injuries, having a substantially cylindrical shield tube and a pair of wings linked to a front end side of the shield tube, a hub inserted into an inner bore of the shield tube such that it can be moved in an axial direction, and a cannula mounted to a front end portion of the hub, so that the cannula can be stored away in the inner bore of the shield tube, covering a front end of the cannula. The wings have wing protrusions protruding from respective wing faces at a base region of the wings. The shield tube has at lease one through hole on its tubular side wall and a front end protrusion formed on its inner circumferential surface, the through hole being positioned so that the wing protrusions can be inserted and the front end protrusion being positioned at an axial position corresponding substantially to the through hole. The hub has a main tubular portion and a holding portion positioned near the front end of the main tubular portion, the holding portion having a large diameter portion whose diameter is larger than that of the main tubular portion so that a step portion is formed by a rear end surface of the large diameter portion. The front end protrusion of the shield tube can be engaged with the step portion of the hub, and in such engaged state the wing protrusions can be engaged with the step portion of the hub by bending the two wings along the shield tube side walls so that the wing protrusions pass through the through hole. With the cannula protruding for a predetermined length from the front end of the shield tube, the hub is held so as not to move inside the shield tube toward the base end by letting the front end protrusion or the wing protrusions engage with the step portion of the hub.

According to this configuration, the respective holding forces for holding the medical needle to the winged shield during the puncturing action and after the puncturing action can be set to the optimum forces.

In this medical needle device, it is preferable that with the two wings being bent along the shield tube side walls so that the wing protrusions are engaged with the step portion of the hub, by pinching the two wings at the position of the wing protrusions and applying a pressure to them, the holding force acting on the hub can be increased beyond the holding force attained by the engagement of the front end protrusion with the step portion of the hub.

It is preferable that the pair of through holes corresponding to a pair of wing protrusions are formed separately on two side walls of the shield tube.

It is preferable that a pair of front end protrusions are formed, and each of the front end protrusions is arranged respectively between the pair of through holes in the inner circumferential direction of the shield tube.

It is preferable that the through hole has the shape of one groove ranging over the two lateral surfaces of the shield tube.

It is preferable that the base region of the wings is thinner than an end region of the wings.

It is preferable that a bottom portion of the outer surface of the shield tube is flat.

It is preferable that the shield tube further includes a rear interlocking portion formed at an inner circumferential surface of a rear end portion of the shield tube, the rear interlocking portion having an inner diameter smaller than that of the large diameter portion of the holding portion of the hub and the rear interlocking portion being provided with an annular groove formed at an intermediate portion in axial direction. By moving the hub with respect to the shield tube toward the rear end in the axial direction, the large diameter portion at the holding portion of the hub can be engaged with the annular groove at the rear interlocking portion of the shield tube. Due to this engagement, the hub is held by the shield tube, with the cannula being stored in the inner bore of the shield tube.

In the medical needle device with the above-described basic configuration, it is preferable that the holding portion of the hub further includes an outward annular protrusion behind the large diameter portion, forming an annular groove in the outer surface of the hub between the large diameter portion and the outward annular protrusion. By engaging the front end protrusion of the shield tube or the wing protrusions with the annular groove in the hub, it is possible to attain a function that is similar to the holding function based on the step portion.

It is preferable that the shield tube further includes a rear interlocking portion formed at an inner circumferential surface of a rear end portion of the shield tube, the rear interlocking portion having an inward annular protrusion. The inward annular protrusion can be engaged with the annular groove of the hub by moving the hub with respect to the shield tube in an axial direction toward the base end. Due to this engagement, the hub is held by the shield tube in a state in which the cannula is stored in the inner bore of the shield tube.

In the medical needle device with the above-described basic configuration, it is preferable that a holding tab is formed on an upper side of the shield tube. By placing a finger on the holding tab, the practitioner can prevent movement of the shield tube during operation so as to facilitate the operation to move the needle or hub in the shield.

It is preferable that the medical needle device further includes an auxiliary holding mechanism provided at a base end portion of the shield tube and an auxiliary holding portion provided at a rear portion of the hub. The auxiliary holding mechanism is composed of a bendable strip attached to the outer surface of the base end portion of the shield tube, an auxiliary protrusion provided at the bendable strip, and a through hole provided in the shield tube wall such that the auxiliary protrusion can be inserted into the inner bore of the shield tube by rotating the bendable strip. The auxiliary holding portion is composed of an auxiliary annular groove or an auxiliary annular protrusion formed in the outer surface of the hub. With the cannula protruding for a predetermined length from the front end of the shield tube, an auxiliary holding force for holding the hub to the shield tube can be applied by engaging the auxiliary protrusion through the through hole with the auxiliary annular groove or auxiliary annular protrusion of the hub.

BEST MODE FOR CARRYING OUT THE INVENTION

Embodiment 1

Figure 1:
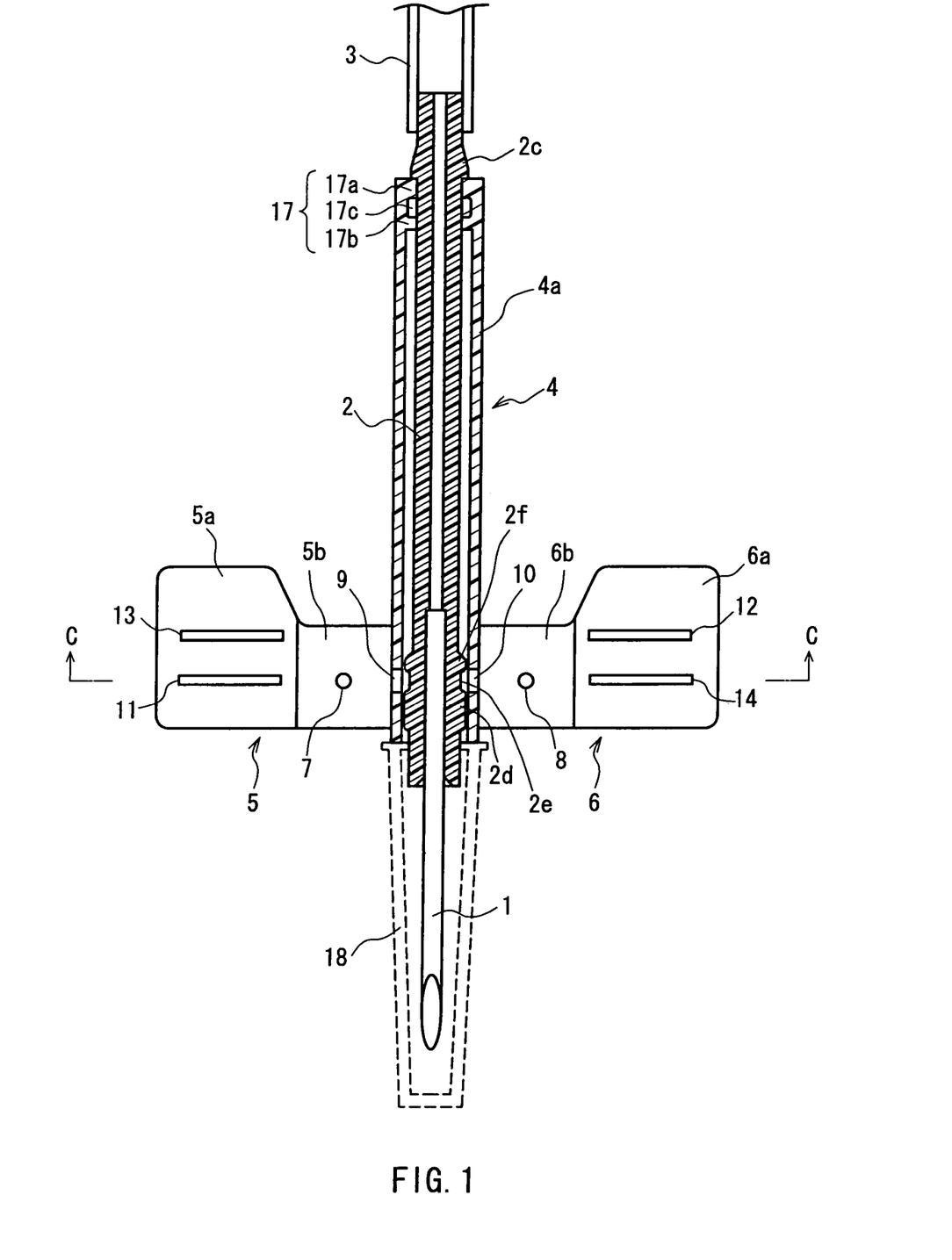
FIG. 1 is a cross-sectional view illustrating the planar shape of a winged medical needle device according to Embodiment 1 of the present invention.

FIG. 1 is a cross-sectional view illustrating the planar shape of a winged medical needle device according to Embodiment 1 of the present invention. Numeral 1 denotes a cannula, which is fastened to the front end portion of a hub 2 made of plastic. A tube 3 is connected to the rear end portion of the hub 2. Numeral 4 denotes a winged shield, made of a shield tube 4a made of plastic and having a substantially cylindrical shape, and left and right wings 5 and 6. The cannula 1 and the hub 2 are inserted into the inner bore of the shield tube 4a, and can be moved in the axial direction. The left and right wings 5 and 6 are provided at the front end portion of the shield tube 4a, that is, at the end on the side from which the cannula 1 protrudes. The wings 5 and 6 are coupled to both sides of the peripheral surface of the shield tube 4a, and may be of symmetric shape with the axis of the shield tube 4a in the center. A needle cap 18 can be mounted to the front end portion of the hub 2, covering the cannula 1.

The wings 5 and 6 may be partitioned into end regions 5a and 6a, and base regions 5b and 6b (linked to the shield tube 4a). Wing protrusions 7 and 8 are formed on the base regions 5b and 6b, respectively. Through holes 9 and 10 are formed in the left and right side walls of the shield tube 4a corresponding to the wing protrusions 7 and 8. Bar-shaped ribs 11 and 12 and grooves 13 and 14 may be formed in the end regions 5a and 6a.

Figure 2A:
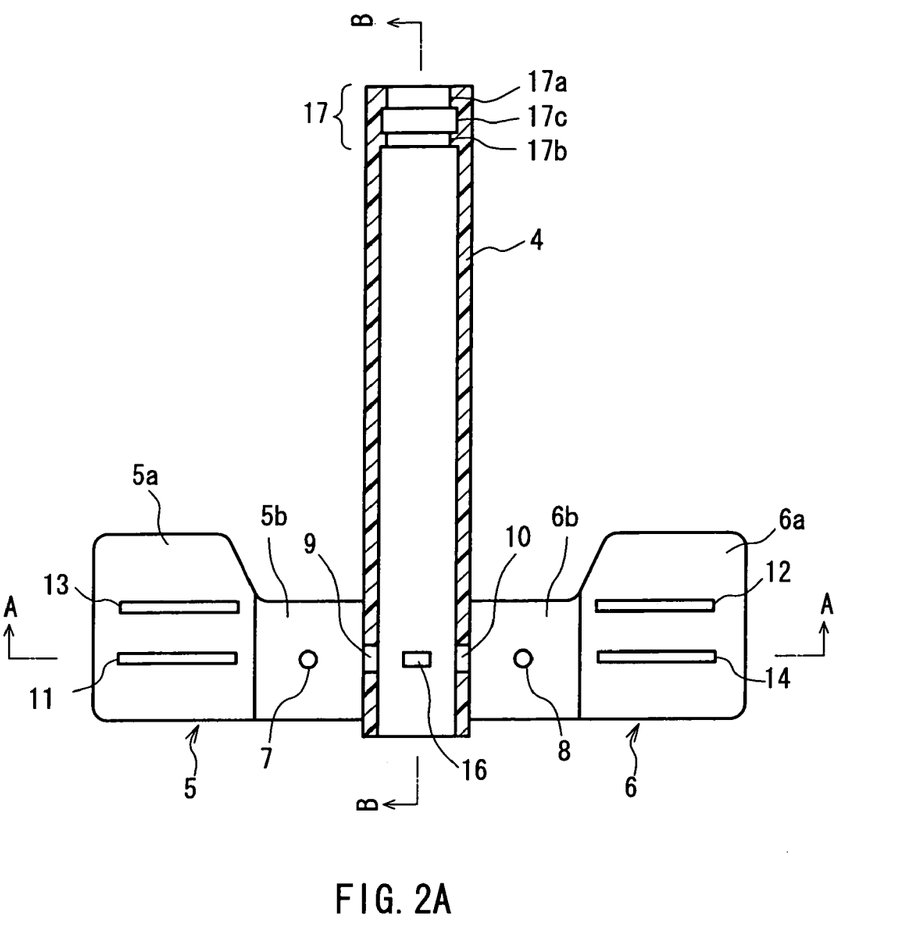
FIG. 2A is a cross-sectional view illustrating the planar shape of the winged shield of the winged medical needle device in FIG. 1.
Figure 2B:
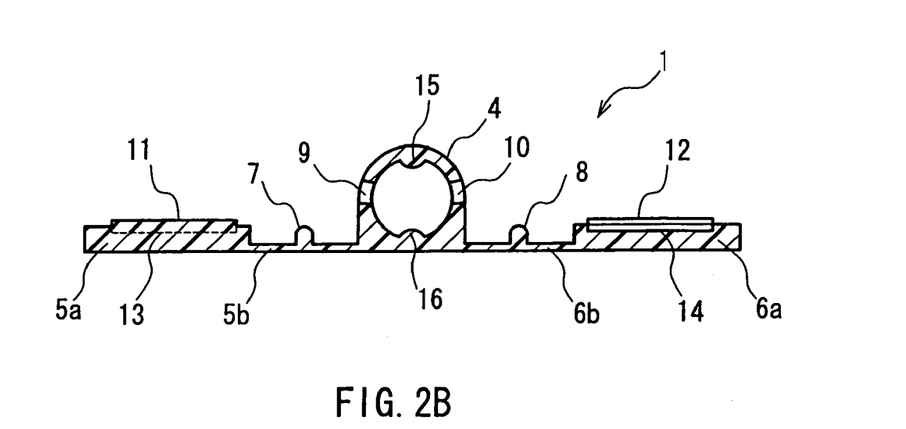
FIG. 2B is a cross-sectional view taken along A-A in FIG. 2A.

FIG. 2A illustrates the cross-sectional shape of the winged shield 4. FIG. 2B shows a cross section along A-A in FIG. 2A. The base regions 5b and 6b of the wings 5 and 6 are thinner than the end regions 5a and 6a. Consequently, the wings 5 and 6 can be bent easily at the base regions 5b and 6b.

Figure 3:
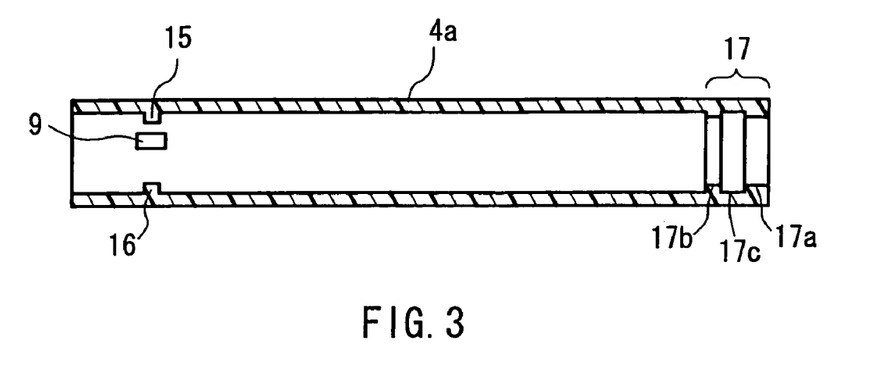
FIG. 3 is a cross-sectional view taken along B-B in FIG. 2A.

FIG. 3 shows a cross section in the axial direction of the shield tube 4a, along B-B in FIG. 2A. Front end protrusions 15 and 16 may be formed at the top and the bottom of the inner surface in the vicinity of the front end of the shield tube 4a. The position in the axial direction of the front end protrusions 15 and 16 coincides approximately with the position of the through holes 9 and 10. A rear end interlocking portion 17 is formed on the inner surface at the rear end of the shield tube 4a. The rear end interlocking portion includes a small diameter portion 17a and an inward annular protrusion 17b formed in the circumferential direction. The inward annular protrusion 17b is formed with a predetermined spacing relative to the small diameter portion 17a, thereby forming an annular groove 17c.

Figure 4A:
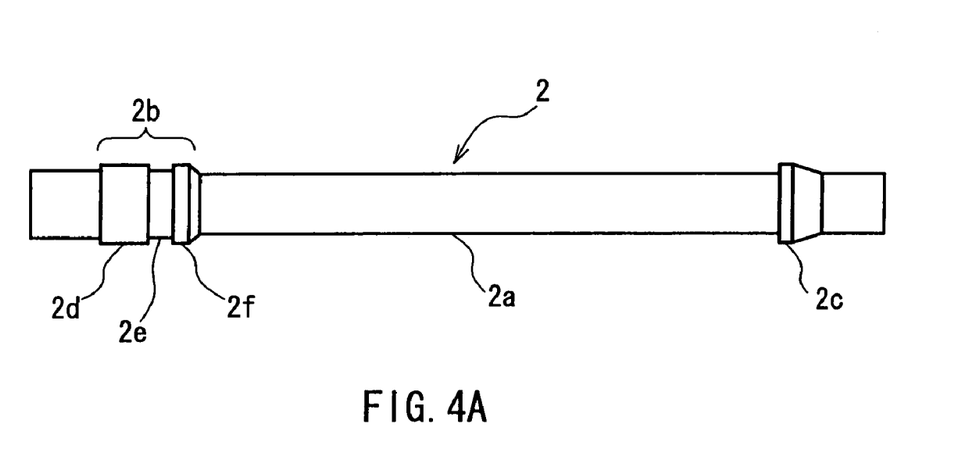
FIG. 4A is a front view of the hub of the winged medical needle device in FIG. 1.
Figure 4B:
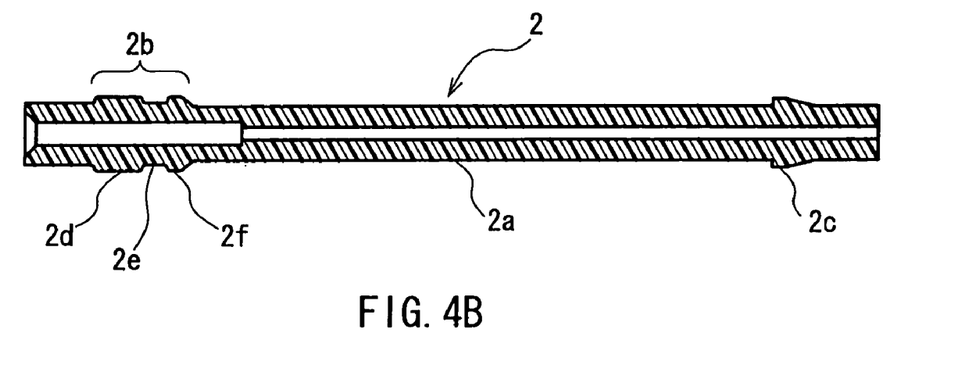
FIG. 4B is a cross-sectional view taken along the axial direction of the hub.

FIG. 4A illustrates the external shape of the hub 2. FIG. 4B is a cross-sectional view taken along the axial direction. The hub 2 includes a main tubular portion 2a at a central portion in the axial direction, a holding portion 2b formed at a front end portion thereof, and a limiting portion 2c formed at a rear end portion. The outer diameter of the main tubular portion 2a is smaller than the inner diameter of the small diameter portion 17a and the inward annular portion 17b of the shield tube 4a. Consequently, over the range in which the main tubular portion 2a faces the small diameter portion 17a and the inward annular protrusion 17b, the shield tube 4a can be freely moved in the axial direction with respect to the hub 2. The portions to the front of the holding portion 2b and to the rear of the limiting portion 2c have the same diameter as the main tubular portion 2a.

The outer diameter of the limiting portion 2c of the hub 2 is larger than the inner diameter of the small diameter portion 17a of the shield tube 4a. Consequently, when the step portion formed at the border between the limiting portion 2c and the main tubular portion 2a abuts against the small diameter portion 17a, that is, the rear end of the shield tube 4a, further movement of the hub 2 toward the front of the shield tube 4a is inhibited. Thus, the cannula 1 is prevented from protruding more than a predetermined length from the shield tube 4a.

The holding portion 2b of the hub 2 is made of a large diameter portion 2d, an annular groove 2e, and an outward annular protrusion 2f The outer diameters of the large diameter portion 2d and the outward annular protrusion 2f are slightly larger than the spacing in the radial direction between the front end protrusions 15 and 16 of the shield tube 4a.

To mount the winged shield 4 on the hub 2, the hub 2 is inserted from the front end of the shield tube 4a, and moved toward the base end. First, the limiting portion 2c abuts against the rear end interlocking portion 17. As shown in the figures, the rear end side of the limiting portion 2c is tapered, so that due to the pliability of the plastic, it can easily pass the rear end interlocking portion 17. Almost at the same time, the outward annular protrusion 2f of the hub 2 abuts against the front end protrusions 15 and 16. By forcefully moving the hub 2 toward the base end, the front end protrusions 15 and 16 are pushed past the outward annular protrusion 2f, and the front end protrusions 15 and 16 are engaged with the annular groove 2e.

As a result of the above, the situation shown in FIG. 1 is achieved. The hub 2 in FIG. 1 is in its usage position, and a state is attained in which the cannula 1 protrudes for a predetermined length from the front end of the shield tube 4a. By the engagement of the front end protrusions 15 and 16 with the annular groove 2e, the hub is prevented from moving in the axial direction within the shield tube 4a, and so the hub 2 is held inside the shield tube 4a. In this situation shown in FIG. 1, further movement of the cannula 1 in axial direction toward the front end is inhibited by the engagement of the limiting portion 2c and the small diameter portion 17a. Consequently, the engagement of the front end protrusions 15 and 16 with the annular groove 2e provides a main function of holding the hub 2 such that it is not moved to the base end of the shield tube 4a.

The holding of the hub 2 in the usage position has the function of preventing accidents after the cannula 1 has been placed on the patient and is retained, such as the cannula 1 moving within the winged shield 4 towards the base end side and being removed from the patient. On the other hand, to dispose of the medical needle device after usage, the cannula 1 is retracted into the shield tube 4a, in order to prevent needle-stick injuries. For this, the hub 2 is moved toward the rear end of the shield tube 4a, so that when the holding force in the usage position is too strong, this action is difficult. Consequently, the holding force in the usage position should be set to a range in which the holding of the hub 2 is not too easily removed, and the action of storing away the cannula 1 is not too difficult.

In this embodiment, the front end protrusions 15 and 16 engaging the annular groove 2e of the hub 2 are partially formed at the top and the bottom on the inner periphery of the shield tube 4a. Thus, the holding force due to the engagement is adjusted to a relatively weak force. However, there is no limitation to restrict the formation range of the front end protrusions 15 and 16 in this way, and it is also possible to adjust the holding force by other configurations, such as by changing the protrusion amount of the front end protrusions 15 and 16.

The outer diameter of the large diameter portion 2d and the outward annular protrusion 2f is larger than the inner diameter of the small diameter portion 17a and the inward annular protrusion 17b of the shield tube 4a. Consequently, when, from the situation in FIG. 1, the hub 2 is moved toward the rear end of the shield 4a, the engagement of the front end protrusions 15 and 16 with the annular groove 2e is released, and when the hub 2 is moved further toward the rear, then the outward annular protrusion 2f first abuts against the inward annular protrusion 17b. Since the outward annular protrusion 2f has a taper at its rear end, as shown in FIG. 4, and since its outer diameter is only slightly larger than the inner diameter of the inward annular protrusion 17b, it easily can be passed by the inward annular protrusion 17b by forcefully moving the hub 2. When the outer annular protrusion 2f passes the inward annular protrusion 17b, the outward annular protrusion 2f engages with the annular groove 17c. Furthermore, the inward annular protrusion 17b engages with the annular groove 2e. Due to this engaging, the axial movement of the hub 2 within the shield tube 4a is inhibited, and a state is achieved in which the hub 2 is held in its storage position within the shield tube 4a. In this storage position, the cannula 1 is stored within the shield tube 4a, and a state is achieved in which needle-stick injuries can be prevented.

The force holding the hub 2 in this storage position should be sufficiently strong, because ordinarily, there is no need to move the hub 2 from the storage state, in which needle-stick injuries are prevented, in the direction in which the cannula 1 is protruded back out, and it is desirable that the hub 2 is held reliably in the storage position. The holding force of the hub 2 in the storage position with the above-described configuration is sufficiently larger than the holding force in the usage position. The reason for this is that, as opposed to the front end protrusions 15 and 16, the engagement between the holding portion 2b of the hub 2 and the rear end interlocking portion 17 of the shield tube 4a is due to an annular protrusion that is formed around the entire internal surface.

The rear end interlocking portion 17 also can have a configuration in which the small diameter portion 17a is substituted by the inward annular protrusion 17b. That is to say, in this configuration, only the inward annular protrusion 17b is formed at the rear end of the shield tube 4a, and no annular groove 17c is formed. In this case, the engagement between the holding portion 2b of the hub 2 and the rear end interlocking portion 17 of the shield tube 4a is performed only by the engagement between the inward annular protrusion 17b and the annular groove 2e.

Figure 5A:
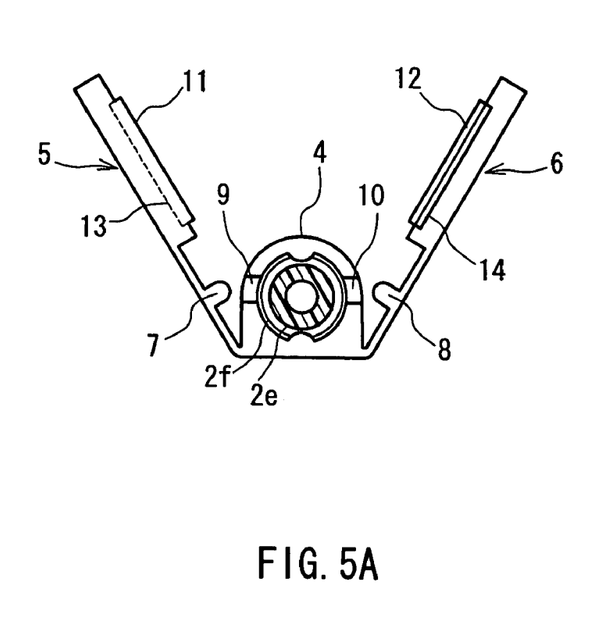
FIGS. 5A to 5C are cross-sectional views illustrating the operation of the winged medical needle device in FIG. 1.
Figure 5B:
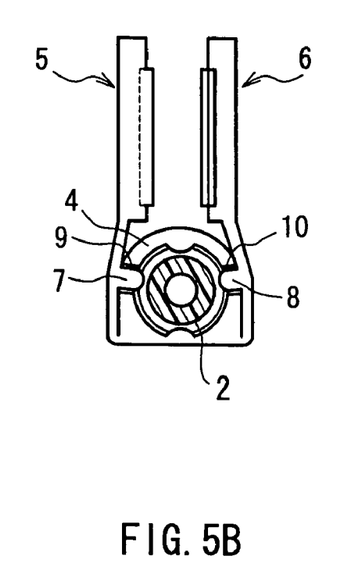
Figure 5C:
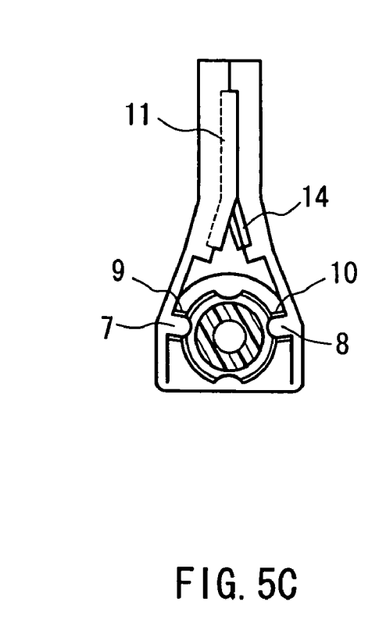

FIGS. 5A to 5C illustrate the function of the wing protrusions 7 and 8 provided on the wings 5 and 6. FIGS. 5A to 5C are cross-sectional views taken along C-C in FIG. 1. However, all hatching besides that of the hub 2 has been omitted to facilitate understanding. The action of using the wings 5 and 6 is carried out in the course of puncturing. For this, it is necessary that the hub 2 is arranged in the usage position shown in FIG. 1, and the annular groove 2e of the hub 2 is in opposition to the through holes 9 and 10. Ordinarily, the medical needle device is used in the situation shown in FIG. 1, and the cannula 1 is in a suitable position with respect to the winged shield 4 during the puncturing, so that it is not necessary to position it during usage. Furthermore, with this embodiment, the situation in FIG. 1 is held by the engagement between the annular groove 2e and the front end protrusions 15 and 16, so that displacement before the puncturing action can be prevented.

As shown in FIG. 5A, when the wings 5 and 6 are lifted upwards along the outer surface of the shield tube 4a, the wing protrusions 7 and 8 oppose the through holes 9 and 10. As shown in FIG. 5B, when the wings 5 and 6 are lifted further upwards, the wing protrusions 7 and 8 are inserted into the through holes 9 and 10, extend through the wall of the shield tube 4a, and protrude into the inner bore. As a result, the front end portions of the wing protrusions 7 and 8 engage with the annular groove 2e of the hub 2. Thus, the hub 2, that is, the cannula 1, is held by the winged shield 4.

As further shown in FIG. 5C, when the two wings 5 and 6 are overlapped, the bar-shaped protrusions 11 and 12 are fitted into the bar-shaped grooves 13 and 14. Thus, the two wings 5 and 6 are overlapped such that there is a predetermined relation between their relative positions. Consequently, even when the wing protrusions 7 and 8 are not properly inserted into the through holes 9 and 10 at the stage shown in FIG. 5B, their relative positions can be corrected and the above-mentioned engagement can be reliably achieved.

For a smooth insertion of the wing protrusions 7 and 8, the relative positions of the wing protrusions 7 and 8 and the through holes 9 and 10 must be set with high precision. Also, as noted above, by providing the base regions 5b and 6b with thin walls, the wings 5 and 6 can be bent more easily along the outer face of the shield tube 4a when they are lifted upwards.

This action is performed in the course of puncturing, so that the holding force of the hub 2 due to the engagement between the wing protrusions 7 and 8 and the annular groove 2e should be sufficiently strong. That is to say, it is necessary that a holding force can act that is stronger than the holding by an engagement between the above-mentioned front end protrusions 15 and 16 and the annular groove 2e. The puncturing action is performed while pressing the two wings 5 and 6 together with one's fingers in a state in which the tips of the wing protrusions 7 and 8 engage the annular groove 2e of the hub 2, so that it is easy to attain a sufficient holding power. However, care needs to be taken that the shape and dimensions of the annular groove 2e and the wing protrusions 7 and 8 are set precisely.

It is preferable that the shape and dimensions of the wing protrusions 7 and 8 are such that they easily can be inserted into the through holes 9 and 10. Furthermore, usability is improved if the diameter of the protrusions 7 and 8 is a little smaller than the diameter of the through holes 9 and 10, so that when the pressure is released, the wing protrusions 7 and 8 immediately are released from the through holes 9 and 10.

In this example, the protrusion 11 and the groove 13 are formed in the wing 5, and the protrusion 12 and the groove 14 are formed in the wing 6, and the protrusion 11 engages the groove 14, whereas the protrusion 12 engages the groove 13, but there is no particular limitation to this combination. For example, it is also possible to form one protrusion on one wing and a corresponding groove on the other wing, or to form two protrusions on one wing and two corresponding grooves on the other wing.

It is preferable that the shape of the inner bore in the shield tube 4a corresponds to the shape of the outer surface of the hub 2. For example, if the cross-sectional profile of the hub 2 perpendicular to its axis is circular, then it is preferable that the inner bore of the shield tube 4a also is circular, or that at least a portion of the inner bore is circular. In this embodiment, the inner bore of the shield tube 4a is circular, but it is also possible that the upper side of the inner bore is provided with a curved surface corresponding to the outer surface shape of the hub 2, and that the bottom portion of the inner bore surface is flat. Furthermore, the bottom portion of the outer surface of the shield tube 4a is made flat. In particular, it is preferable that the bottom portion of the outer surface of the shield 4a is made flat, so that it can be positioned securely on the patient's skin.

Regarding the dimensions of the shield tube, it is needless to say that its length should be such that the tip of the cannula can be stored completely away, but there are no particular limitations regarding the other dimensions. Preferably, the diameter of the inner bore of the shield tube is slightly larger than the maximum outer diameter of the hub. For example, it can be configured such that the maximum diameter portion of the hub just about touches the inner bore surface of the shield tube, and the hub and the cannula can be moved in the axial direction within the shield tube inner bore by sliding.

The following is an explanation of the usage method of the medical needle device of this embodiment. For use, as shown in FIG. 1, the winged shield 4 is mounted on the hub 2 to which the cannula 1 has been attached, and the medical needle device is taken with the needle cap 18 covering the cannula 1. The practitioner takes the two wings 5 and 6, holding them together with one hand, and removes the needle cap 18 from the cannula 1 with the other hand. Next, as shown in FIG. 5B and 5C, the two wings are lifted up, grasping the wings 5 and 6 at the portion of the wing protrusions 7 and 8. In this situation, the wing protrusions 7 and 8 are passed through the through holes 9 and 10, and engage the annular groove 2e of the hub 2. Consequently, the cannula 1 and the hub 2 are held so that they cannot move freely within the shield tube 4a. In this situation, the cannula 1 is set on the patient.

When the cannula 1 has been set on the patient, the two wings 5 and 6 that had been overlapping are spread apart, and are fastened with adhesive tape on the patient's skin. In this situation, the wing protrusions 7 and 8 are not engaged with the hub 2, but the front end protrusions 15 and 16 of the shield tube 4a are engaged with the annular groove 2e of the hub 2, and the holding force is weaker than when using the wings 5 and 6, but the hub 2 is held inside the shield tube 4a. Consequently, the cannula 1 moving in the axial direction toward the base end within the shield tube 4a, thus removing the cannula 1 from the patient's body, can be prevented.

When the infusion of the drug solution or the like into the patient's body has been finished, the tube 3 is pulled in the base end direction of the shield tube 4a, with the wings 5 and 6 still fastened in place, or while pressing down the wings 5 and 6 by hand. This releases the engagement between the front end protrusions 15 and 16 and the annular groove 2e, whose holding force is weak, and the base end 2 becomes movable. Moreover, when the tube 3 is pulled in the direction of the base end, the cannula 1 is stored all the way to its front end portion inside the shield tube 4a, and a state is attained in which needle-stick injuries can be prevented. At the same time, the holding portion 2b of the hub 2 engages with the rear interlocking portion 17 of the shield tube 4a, and the hub 2 is held firmly in the storage position inside the shield tube 4a.

Embodiment 2

Figure 6:
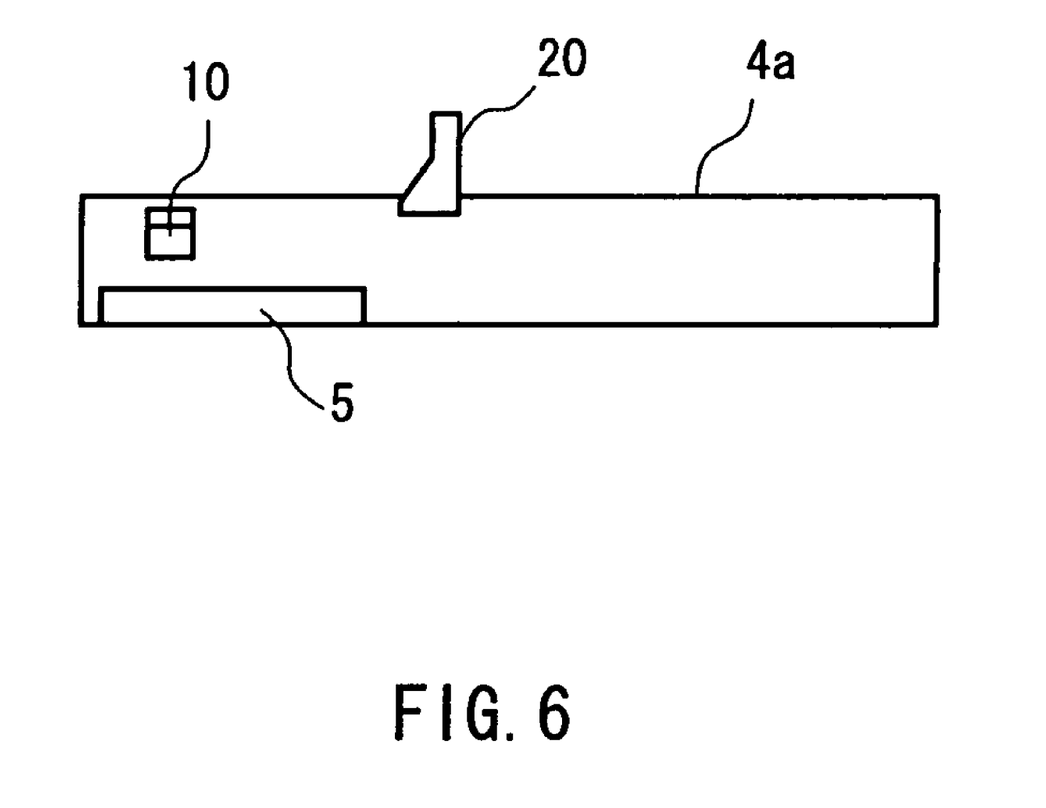
FIG. 6 is a lateral view of the winged shield of a winged medical needle device according to Embodiment 2 of the present invention.

FIG. 6 shows a winged shield that is part of a medical needle device according to Embodiment 2. In addition to the configuration of Embodiment 1, this winged shield is provided with a holding tab 20 at the upper surface of the shield tube 4a. As mentioned above, after using the medical needle device, the tube connected to the hub is pulled in the direction of the base end of the shield tube 4a, and the hub is held inside the shield tube 4a in a position preventing needle-stick injuries. For this, the holding tab 20 is used to fasten the shield tube 4a so that it cannot be moved. That is to say, by placing a finger on the holding tab 20 and countering the force pulling the tube, the action of pulling the hub in the direction of the base end of the shield tube 4a is facilitated.

Embodiment 3

Figure 7A:
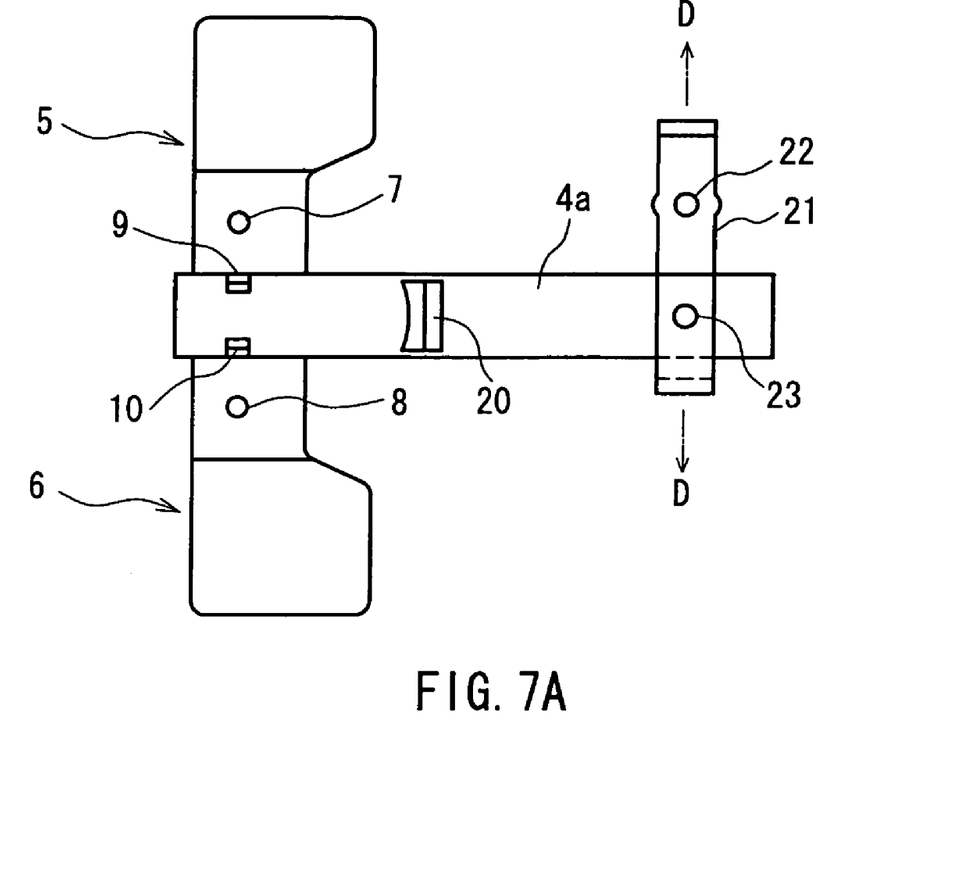
FIG. 7A is a plan view of the winged shield of a winged medical needle device according to Embodiment 3 of the present invention.
Figure 7B:
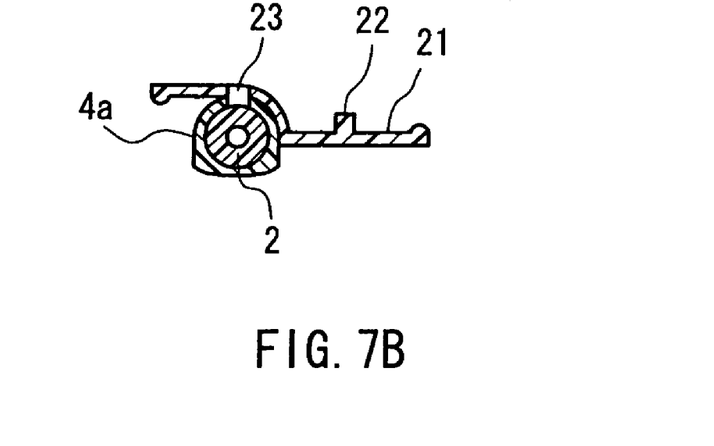
FIG. 7B is a cross-sectional view taken along D-D in FIG. 7A.

FIG. 7 shows a winged shield that is part of a medical needle device according to Embodiment 3. In addition to the configuration of Embodiment 1, this winged shield is provided with a supplemental holding mechanism including a bendable strip 21 at the base end portion of the shield tube 4A. FIG. 7A is a plan view thereof, and FIG. 7B is a cross-sectional view along D-D in FIG. 7A. The bendable strip 21 is fastened to the shield tube 4a on one side in its longitudinal direction. The other side can be rotated around the axis of the shield tube 4a, and has a protrusion 22. The fastened portion is provided with a through hole 23. The tubular wall of the shield portion 4a is provided with a through hole that is linked to the through hole 23.

Figure 8:
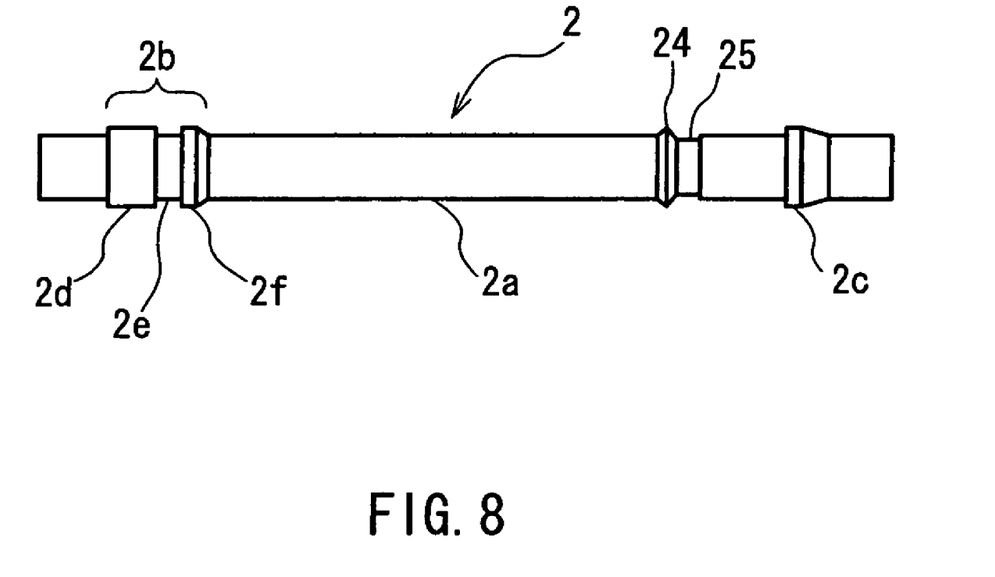
FIG. 8 is a front view of the hub of a winged medical needle device according to Embodiment 3 of the present invention.

FIG. 8 shows the hub 2, which is used in combination with the shield tube 4a shown in FIG. 7. The rear portion of the hub 2 is provided with a supplementary holding portion made of an annular protrusion 24 and an annular groove 25. This hub 2 is inserted into the winged shield of FIG. 7, and with the limiting portion 2c abutting the base end of the shield tube 4a, that is, in the above-described usage state, the position of the annular groove 25 of the supplementary holding portion coincides with the position of the through hole 23 of the bendable strip 21.

In this situation, by wrapping the bendable strip 21 and inserting the protrusion 22 into the through hole 23, the front end of the protrusion 22 engages the annular groove 25. Thereby, a holding force can be applied that holds the hub 2 with respect to the shield tube 4a. This holding force is applied supplementarily in addition to the holding force attained by the engagement of the front end protrusions 15 and 16 of the shield tube 4a with the annular groove 2e of the hub 2. If no supplementary holding force is needed, or when the hub 2 is stored in the shield tube 4a after usage, then the protrusion 22 of the bendable strip 21 is removed from the through hole 23.

If the diameters of the protrusion 22 and the through hole 23 are set appropriately, and the protrusion 22 is press-fitted into the through hole 23, then it is possible to fix this state. Furthermore, it is also possible to attain a similar holding function with only one of the annular protrusion 24 and the annular groove 25.

With the above embodiment, the relatively weak holding force after the puncturing action can be supplemented, and different holding forces can be achieved during needle retention and during needle storage, so that holding forces of two levels can be set.

Embodiment 4

Figure 9:
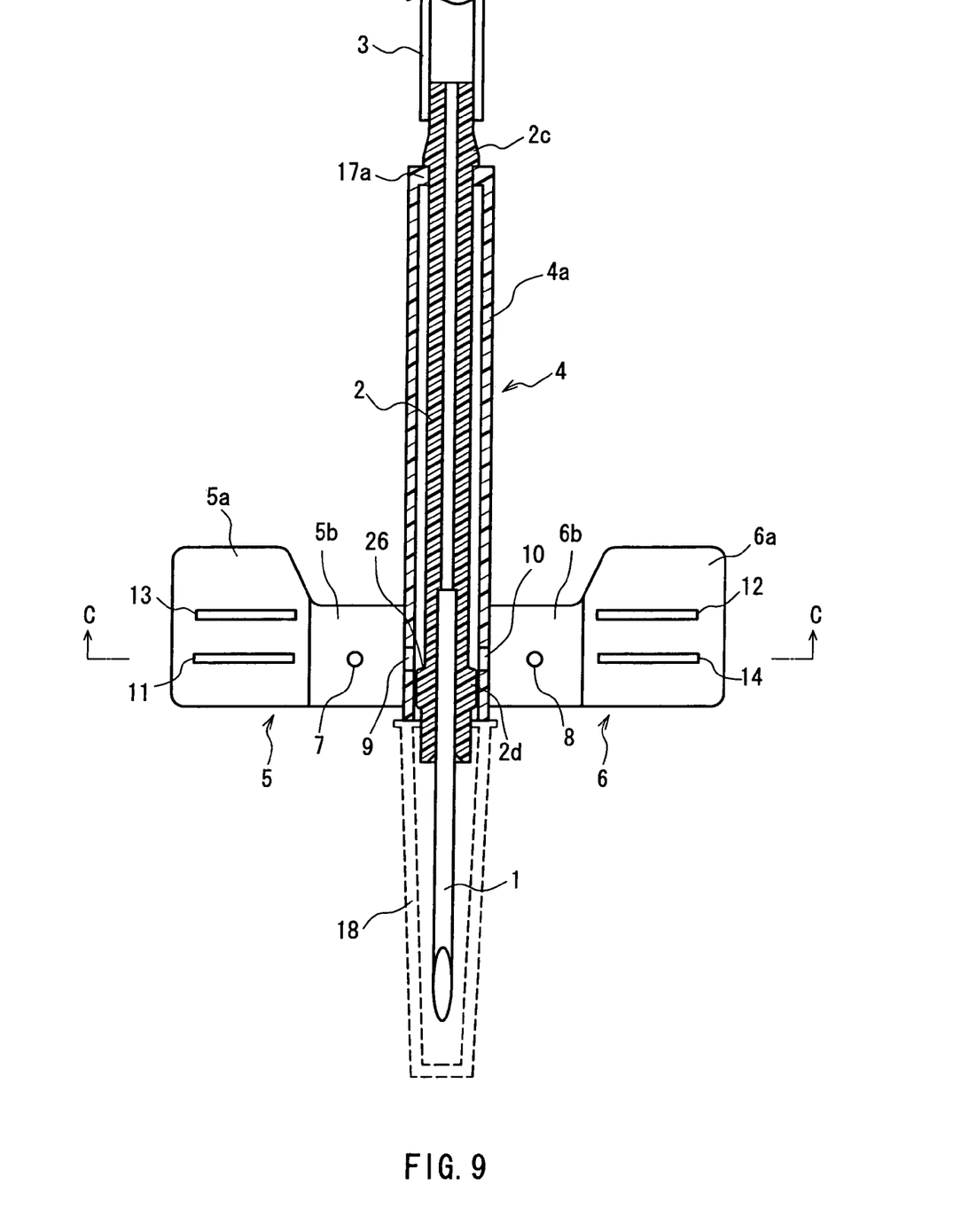
FIG. 9 is a cross-sectional view illustrating the planar shape of a winged medical needle device according to Embodiment 4 of the present invention.

FIG. 9 shows a medical needle device according to Embodiment 4. In this device, the holding portion of the hub 2 is made of only a large diameter portion 2d. The rear end portion of the shield tube 4a is provided only with a small diameter portion 17a. The rest of the configuration is the same as in Embodiment 1.

With this configuration, the holding effect during usage is attained by the step portion 26 that is formed at the border of the large diameter portion 2d of the hub 2 and the portion to the rear of it. That is to say, by engaging the wing protrusions 7 and 8 or the front protrusions (not shown in FIG. 9) of the shield tube 4a with the step portion 26, the hub 2 is prevented from moving from the position shown in the figure toward the rear end of the shield tube 4a. Thus, as in Embodiment 1, the hub 2 can be held by the wing protrusions 7 and 8 during the puncturing action, and it can be held by the front protrusions of the shield tube 4a after the puncturing action.

FIG. 9 does not show a structure in which the hub 2 is held in its stored state, but such a holding effect can be attained with any suitable known structure.

Embodiment 5

Figure 10:
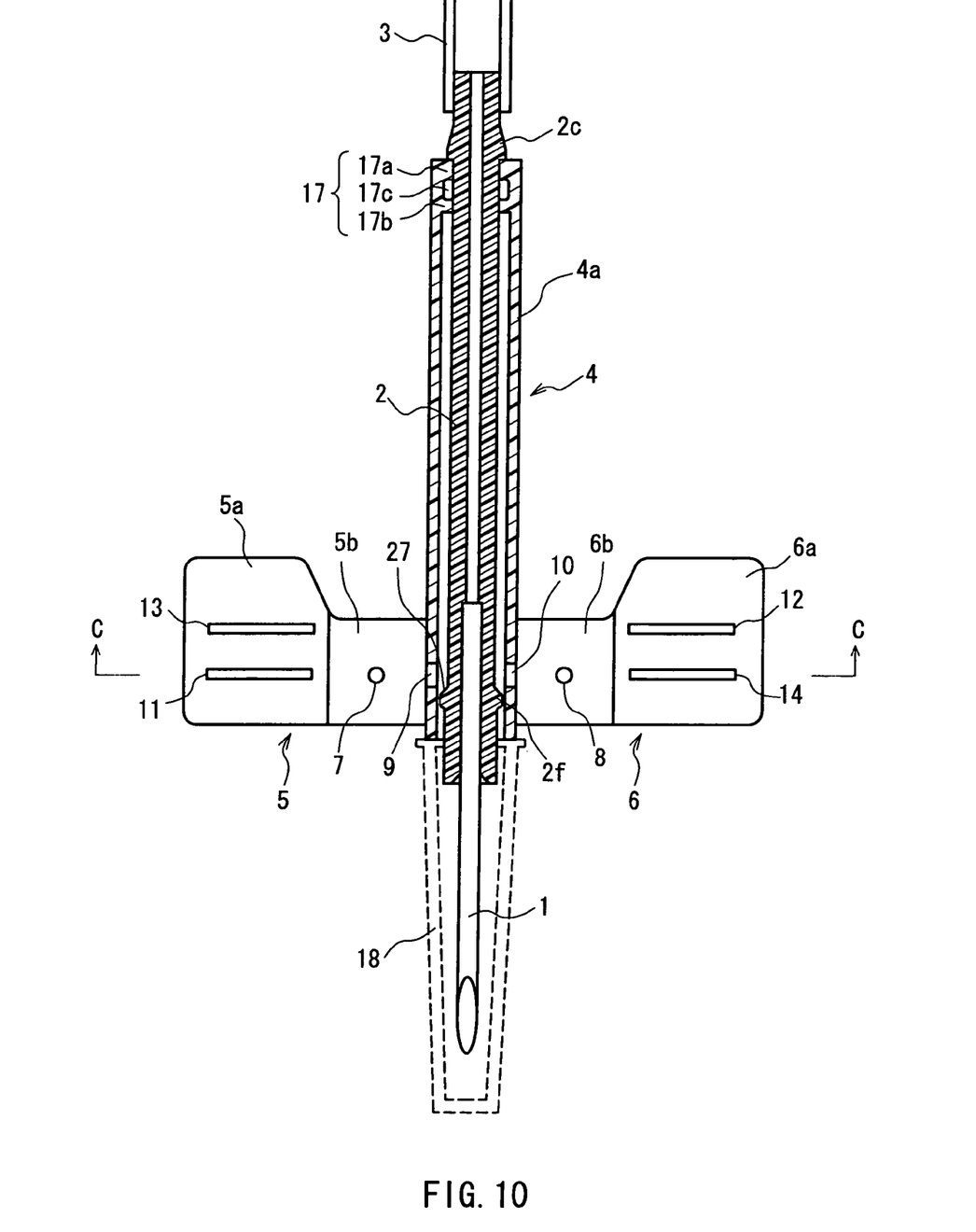
FIG. 10 is a cross-sectional view illustrating the planar shape of a winged medical needle device according to Embodiment 5 of the present invention.

FIG. 10 shows a medical needle device according to Embodiment 5. In this device, the holding portion of the hub 2 is made only of the outward annular protrusion 2f The outward annular protrusion 2f is arranged in substitution for the large diameter portion 2d in FIG. 1. The rest of the configuration is the same as in Embodiment 1.

In this configuration, the holding effect is attained by a step portion 27 formed at the border between the outward annular protrusion 2f of the hub 2 and the portion to the rear of it. That is to say, by engaging the wing protrusions 7 and 8 or the front protrusions (not shown in FIG. 10) of the shield tube 4a with the step portion 27, the hub 2 is prevented from moving from the position shown in the figure toward the rear end of the shield tube 4a. Thus, as in Embodiment 1, the hub 2 can be held by the wing protrusions 7 and 8 during the puncturing action, and it can be held by the front protrusions of the shield tube 4a after the puncturing action.

Furthermore, in a state in which the hub 2 is stored away, the outward annular protrusion 2f engages the annular groove 17c formed in the rear end interlocking portion 17 of the shield tube 4a. Thus, the hub 2 can be held in its stored state.

INDUSTRIAL APPLICABILITY

With the present invention, a medical needle device can be obtained, in which the holding force for holding a medical needle against a winged shield is set to the optimum force both during the puncturing action and after the puncturing action. Thus, the medical needle can be held securely during the puncturing action, the medical needle easily can be moved to a storage position after usage,. and by storing the medical needle in a position within the winged shield in which needle-stick injuries can be prevented, the action of holding this state can be performed safely and with ease.

What is claimed is:

1. A medical needle device comprising: a winged shield for reduction of needle-stick injuries having a substantially cylindrical shield tube and a pair of wings linked to a front end side of the shield tube; a hub inserted into an inner bore of the shield tube such that it can be moved in an axial direction; and a cannula mounted to a front end portion of the hub, so that the cannula can be stored away in the inner bore of the shield tube, covering a front end of the cannula, wherein the wings have wing protrusions protruding from respective wing faces at a base region of the wings, the shield tube has a pair of through holes formed separately on both sides of its tubular wall and a pair of a front end protrusions formed on its inner circumferential surface, each through hole being positioned so that one wing protrusion can be inserted and each of the front end protrusions being positioned at an axial position corresponding substantially to the through hole and arranged between the pair of through holes in the circumferential direction of the shield tube and the hub has a main tubular portion and a holding portion positioned near the front end of the main tubular portion, the holding portion having a large diameter portion whose diameter is larger than that of the main tubular portion so that step portion is formed by a rear end surface of the large diameter portion;

wherein the front end protrusions of the shield tube can be engaged with the step portion of the hub, and in such engaged state the wing protrusions can be engaged with the step portion of the hub by bending the two wings along the shield tube side walls so that the wing protrusions pass through the through hole; and wherein with the cannula protruding for a predetermined length from the front end of the shield tube, the hub is held so as not to move inside the shield tube toward the base end by letting the front end protrusion or the wing protrusions engage with the step portion of the hub.

2. The medical needle device according to claim 1, wherein with the two wings being bent along the shield tube side walls so that the wing protrusions are engaged with the step portion of the hub, by pinching the two wings at the position of the wing protrusions and applying a pressure to them, the holding force acting on the hub can be increased beyond the holding force attained by the engagement of the front end protrusions with the step portion of the hub.

3. The medical needle device according to claim 1, wherein each through hole has the shape of one groove ranging over the two lateral surfaces of the shield tube.

4. The medical needle device according to claim 1, wherein the base region of the wings is thinner than an end region of the wings.

5. The medical needle device according to claim 1, wherein a bottom portion of the outer surface of the shield tube is flat.

6. The medical needle device according to claim 1, wherein the shield tube further comprises a rear interlocking portion formed at an inner circumferential surface of a rear end portion of the shield tube, the rear interlocking portion having an inner diameter smaller than that of the large diameter portion of the holding portion of the hub and the rear interlocking portion being provided with an annular groove formed at an intermediate portion in axial direction; and wherein by moving the hub with respect to the shield tube toward the rear end in axial direction, the large diameter portion at the holding portion of the hub can be engaged with the annular groove at the rear interlocking portion of the shield tube, and due to this engagement, the hub is held by the shield tube, with the cannula being stored in the inner bore of the shield tube.

7. The medical needle device according to claim 1, wherein the holding portion of the hub further comprises an outward annular protrusion behind the large diameter portion, forming an annular groove in the outer surface of the hub between the large diameter portion and the outward annular protrusion; and wherein by engaging the front end protrusion of the shield tube or the wing protrusions with the annular groove in the hub, it is possible to attain a function that is similar to the holding function based on the step portion.

8. The medical needle device according to claim 7, wherein the shield tube further comprises a rear interlocking portion formed at an inner circumferential surface of a rear end portion of the shield tube, the rear interlocking portion having an inward annular protrusion, wherein the inward annular protrusion can be engaged with the annular groove of the hub by moving the hub with respect to the shield tube in an axial direction toward the base end, and due to this engagement, the hub is held by the shield tube in a state in which the cannula is stored in the inner bore of the shield tube.

9. The medical needle device according to claim 1, wherein a holding tab is formed on an upper side of the shield tube.

10. The medical needle device according to claim 1, further comprising: an auxiliary holding mechanism provided at a base end portion of the shield tube; and an auxiliary holding portion provided at a rear portion of the hub;

wherein the auxiliary holding mechanism is composed of a bendable strip attached to the outer surface of the base end portion of the shield tube, an auxiliary protrusion provided at the bendable strip, and a through hole provided in the shield tube wall such that the auxiliary protrusion can be inserted into the inner bore of the shield tube by wrapping the bendable strip, and the auxiliary holding portion is composed of an auxiliary annular groove or an auxiliary annular protrusion formed in the outer surface of the hub, and wherein with the cannula protruding for a predetermined length from the front end of the shield tube, an auxiliary holding force for holding the hub to the shield tube can be applied by engaging the auxiliary protrusion through the through hole with the auxiliary annular groove or auxiliary annular protrusion of the hub.

* * * * *